United States Patent
Wang

(10) Patent No.: US 7,385,696 B2
(45) Date of Patent: Jun. 10, 2008

(54) BIREFRINGENCE MEASUREMENT OF POLYMERIC FILMS AND THE LIKE

(75) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 0 days.

(21) Appl. No.: 11/379,373

(22) Filed: Apr. 19, 2006

(65) Prior Publication Data

US 2006/0187452 A1    Aug. 24, 2006

Related U.S. Application Data

(63) Continuation of application No. PCT/US2005/038192, filed on Oct. 24, 2005.

(60) Provisional application No. 60/621,994, filed on Oct. 25, 2004.

(51) Int. Cl.
*G01J 4/00* (2006.01)

(52) U.S. Cl. .................... 356/365; 356/364
(58) Field of Classification Search .......... 356/364, 356/365
See application file for complete search history.

(56) References Cited

U.S. PATENT DOCUMENTS

| 5,521,705 | A | 5/1996 | Oldenbourg et al. |
| 6,473,179 | B1 | 10/2002 | Wang |
| 6,985,227 | B2 | 1/2006 | Wang |
| 2004/0233434 | A1* | 11/2004 | Wang .................. 356/365 |

* cited by examiner

*Primary Examiner*—Roy M Punnoose
(74) *Attorney, Agent, or Firm*—Hancock Hughey LLP

(57) ABSTRACT

Provided are methods for determining the birefringence level of optical material such as polymeric film. In one embodiment, the method uses a setup of optical components that has known system reference angle. The sample may be a stretched polymeric film that has a fast axis angle that has a predetermined orientation in the sample. The system is operated to align the direction of the fast axis of the sample with the reference angle of the system and to measure the birefringence level at a location of the sample. As one aspect of the invention, embodiments and methods are described for accurately determining birefringence levels across a very wide range and up to tens of thousands of nanometers.

24 Claims, 4 Drawing Sheets

BIREFRINGENCE MEASUREMENT OF POLYMERIC FILMS AND THE LIKE

TECHNICAL FIELD

This application relates to precise measurement of birefringence in optical material such as polymeric films.

BACKGROUND

Thin polymeric films are formed of thermoplastic polymers that are made into sheets using any of a variety of processes, such as film extrusion. The polymeric films have a multitude of applications, such as packaging, magnetic media coatings, etc. The polymer may be "oriented" during formation of the film. One technique produces what is commonly referred to as "stretched polymer film," whereby the long polymer molecules are substantially aligned in one direction. Stretching the film improves its physical properties, such as its stiffness and dimensional stability. Stretching also improves a film's optical properties and vapor-barrier effectiveness. There are other ways of orienting polymeric material. For example, photoalignment processes may be employed, whereby polymer alignment results from irradiation of a polymeric film with ultraviolet light.

Polymeric films have birefringence properties that are described in more detail below. In short, the measure of the film's birefringence properties can yield useful insights into the physical, optical, or other properties of the film. For example, the measured level of birefringence in a polymer film can be readily correlated to the extent of polymer orientation or stretch that the film possesses and, therefore, correlated to a desired physical property in the film.

Birefringence means that different linear polarizations of light travel at different speeds through a light-transmissive element such as polymeric film. Retardation or retardance represents the integrated effect of birefringence acting along the path of a light beam traversing the film. If the incident light beam is linearly polarized, two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm).

Oftentimes, the term "birefringence" is interchangeably used with and carries the same meaning as the term "retardance." Thus, unless stated otherwise, those terms are also interchangeably used below.

The two orthogonal polarization components described above are parallel to two orthogonal axes, which are characteristic of the measured portion of the polymeric film sample and are respectively referred to as the "fast axis" and the "slow axis." The fast axis is the axis of the polymeric film that aligns with the faster moving component of the polarized light through the sample. Therefore, a complete description of the retardance of a polymeric film sample along a given optical path requires specifying both the magnitude of the retardance and the relative angular orientation of the fast (or slow) axis of the sample. Oriented (stretched) polymeric film will have an axis that corresponds to the orientation direction of the polymers and that, in turn, corresponds to either the "fast" or "slow" axis described above. This fact can be exploited for simplifying the measure of retardance in the stretched polymeric film and for quickly determining the very high levels of retardance that can be present in such films.

SUMMARY OF THE INVENTION

The present invention is directed to systems and methods for precisely measuring birefringence properties of polymeric films, including stretched polymeric films. Other polymers, such as disc shaped ones, have configurations such that the polymers will exhibit birefringence properties that are amenable to the measurement techniques described here and, therefore, what is described below is not intended to be limited to the long, rod-like polymers mentioned in connection with the preferred embodiment of the invention.

The method uses a setup of optical components that has a known system reference angle. In one embodiment, the polymeric sample has a fast axis angle that has a predetermined orientation in the sample. The system is operated to align the direction of the fast axis of the polymeric sample with the reference angle of the system and to measure the birefringence level at a location on the sample.

As one aspect of the invention, embodiments and methods are described for accurately determining birefringence levels across a very wide range and up to tens of thousands of nanometers.

Other advantages and features of the present invention will become clear upon study of the following portion of this specification and drawings.

DESCRIPTION OF PREFERRED EMBODIMENTS

One preferred embodiment of the present invention uses an optical setup that includes two photoelastic modulators (PEM) to measure linear birefringence in a polymeric film. This setup will be hereafter referred to as a dual PEM setup. This embodiment determines birefringence properties (both magnitude and angular orientation) of the polymeric film. This embodiment is particularly useful for measuring low-level linear birefringence with a very high sensitivity.

It is noted that the system described here is not limited to measurement of birefringence properties of polymeric films. One of ordinary skill will understand that the present system will also permit measure of such properties in any of a variety of optical materials, including single-crystal material such as quartz, calcite, mica, and sapphire. The birefringence may be induced by external forces or intrinsic to the material.

Figure 1:
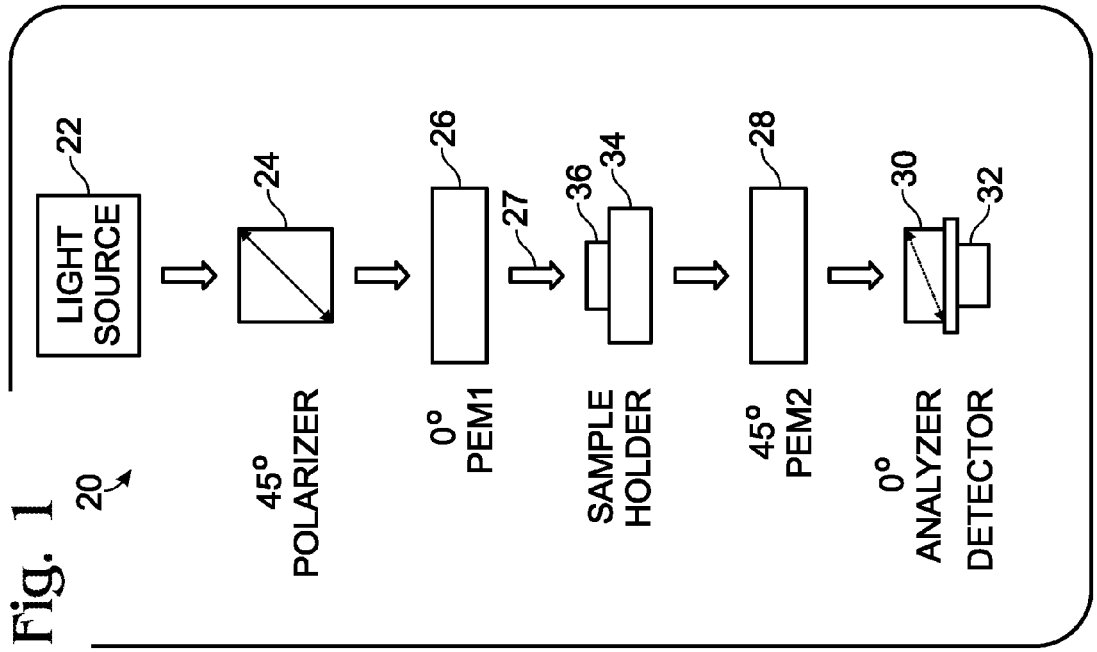
FIG. 1 is a diagram of one preferred embodiment of the present invention showing a preferred arrangement of the optical components of a system for measuring birefringence of polymeric films.

With reference to FIG. 1, the dual-PEM setup 20 of this embodiment generally comprises three modules. The top module includes a light source 22, a polarizer 24 oriented at 45 degrees, and a PEM 26 oriented at 0 degrees.

The bottom module includes a second PEM 28 that is set to a modulation frequency that is different from the modulation frequency of the first PEM 26. The second PEM 28 is oriented at 45 degrees. The bottom module also includes an analyzer 30 at 0 degrees and a detector 32.

The middle module includes a sample support 34, which can be any of a variety of mechanisms for supporting a polymeric film in position between the top and bottom modules to allow a light beam 27 from the source 22 of the setup to pass through the film sample as described more below. The sample support 34 may be of a type that mounts to a computer-controlled, movable X-Y stage to allow the scan of a polymeric film sample 36. The thickness of the sample is shown greatly exaggerated in FIG. 1.

Alternatively, the sample support 34 may be part of or adjacent to the polymeric film production process. For example, the support 34 may be a stationary frame, edge rollers, or conveyor that supports the film for movement of the film across the path of the light beam 27. The support 34 may have a width that supports and exposes a wide sheet of film to the beam. The above-mentioned top and bottom modules of the setup 20 can be supported for synchronized, reciprocating movement across the width of the film, with the film advanced between the modules. It is contemplated that the film could be advanced after each scan of the top and bottom modules, or the film could be continuously moved while the beam, too, is moved.

It is also contemplated that the setup 20 could be configured to provide a number of beams 27 so that several birefringence measurements can be simultaneously made at spaced apart locations across the width of the moving film. This arrangement would enhance the speed with which the birefringence data is collected. It is also contemplated that the components directing the numerous beams (as well as the associated detection components) could be supported for reciprocating motion across the moving or stationary film.

This embodiment (FIGS. 1 and 2) employs as a light source 22 a polarized He—Ne laser having a wavelength of 632.8 nm. The polarizer 24 and analyzer 30 are each a Glan-Thompson-type polarizer. A Si-photodiode detector 32 is used in this embodiment. Both of the PEMs 26, 28 have bar-shaped, fused silica optical elements that are driven by an attached quartz piezoelectric transducers. The two PEMs 26, 28 have nominal resonant frequencies of approximately 50 and 60 KHz, respectively.

Figure 2:
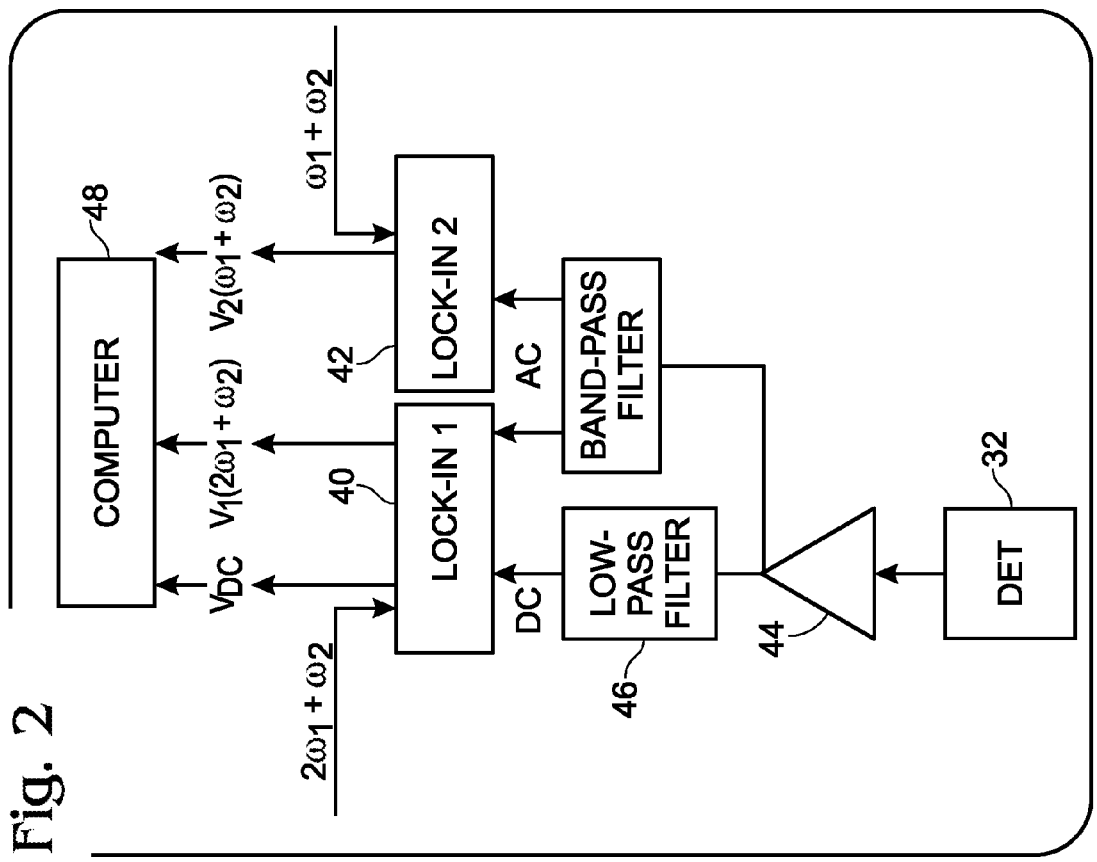
FIG. 2 is a block diagram of the processing components of the system depicted in FIG. 1.

With reference to FIG. 2, the electronic signals generated at the detector 32 contain both "AC" and "DC" signals and are processed differently. The AC signals are applied to two lock-in amplifiers 40, 42. Each lock-in amplifier is referenced at a desired modulation frequency that is a combination of the fundamental modulation frequencies of the two PEMs, and each lock-in amplifier demodulates the signal at that desired modulation frequency provided by the detector 32.

The DC signal is recorded after the signal from detector 32 passes through an analog-to-digital converter 44 and a low-pass electronic filter 46. The DC signal represents the average light intensity reaching the detector 32.

The theoretical analysis underlying the measurement of the birefringence properties of the polymeric film sample 36 is based on a Mueller matrix analysis that is applicable to any retardance-inducing optical element, and is discussed next.

For clarity, the Mueller matrices for three of the optical components in FIG. 1 are shown below. The film sample 36 in the optical arrangement, with a retardation magnitude, $\delta$, and an angle of the fast axis, $\rho$, has the following form:

$$\begin{bmatrix} 1 & 0 & 0 & 0 \\ 0 & \cos(4\rho)\sin^2\left(\frac{\delta}{2}\right) + \sin(4\rho)\sin^2\left(\frac{\delta}{2}\right) & & -\sin(2\rho)\sin\delta \\ & \cos^2\left(\frac{\delta}{2}\right) & & \\ 0 & \sin(4\rho)\sin^2\left(\frac{\delta}{2}\right) & -\left(\cos(4\rho)\sin^2\left(\frac{\delta}{2}\right)\right) + & \cos(2\rho)\sin\delta \\ & & \cos^2\left(\frac{\delta}{2}\right) & \\ 0 & \sin(2\rho)\sin\delta & -\cos(2\rho)\sin\delta & \cos\delta \end{bmatrix}$$

The Mueller matrices of the two PEMs 26, 28, with their retardation axes oriented at 0° and 45° are, respectively:

$$\begin{pmatrix} 1 & 0 & 0 & 0 \\ 0 & 1 & 0 & 0 \\ 0 & 0 & \cos(\delta 1) & \sin(\delta 1) \\ 0 & 0 & -\sin(\delta 1) & \cos(\delta 1) \end{pmatrix} \begin{pmatrix} 1 & 0 & 0 & 0 \\ 0 & \cos(\delta 2) & 0 & -\sin(\delta 2) \\ 0 & 0 & 1 & 0 \\ 0 & \sin(\delta 2) & 0 & \cos(\delta 2) \end{pmatrix}$$

where $\delta 1$ and $\delta 2$ are the time varying phase retardation of the first PEM 26 and second PEM 28 ($\delta 1 = \delta 1_o \sin \omega_1 t$ and $\delta 2 = \delta 2_o \sin \omega_2 t$; where $\omega_1$ and $\omega_2$ are PEMs' modulating frequencies; $\delta 1_o$ and $\delta 2_o$ are the respective retardation amplitudes of the two PEMs).

Using the Mueller matrices of the optical components in the set-up shown in FIG. 1, the light intensity reaching the detector 32 is obtained as follows:

$$\frac{KI_0}{2}\left\{1 + \cos(\delta 1)\cos(\delta 2)\sin(4\rho)\sin^2\left(\frac{\delta}{2}\right) + \sin(\delta 1)\sin(\delta 2)\cos\delta + \right.$$
$$\left. \cos(\delta 1)\sin(\delta 2)\cos(2\rho)\sin\delta + \sin(\delta 1)\cos(\delta 2)\sin(2\rho)\sin\delta\right\} \quad \text{Eqn. (1)}$$

where $I_0$ is the light intensity after the polarizer 24 and K is a constant that represents the transmission efficiency of the optical system after the polarizer.

The functions of $\sin \delta 1$ and $\cos \delta 1$ in equation 1 can be expanded with the Bessel functions of the first kind:

$$\sin\delta 1 = \sin(\delta 1_0 \sin(\omega_1 t)) = \sum_{2k+1} 2J_{2k+1}(\delta 1_0)\sin((2k+1)\omega_1 t) \quad \text{Eqn. (2)}$$

where k is either "0" or a positive integer, and $J_{2k+1}$ is the $(2k+1)^{th}$ order of the Bessel function; and $$\cos\delta 1 = \cos(\delta 1_0 \sin(\omega_1 t)) = J_0(\delta 1_0) + \sum_{2k} 2J_{2k}(\delta 1_0)\cos((2k)\omega_1 t) \quad \text{Eqn. (3)}$$

where $J_0$ is the $0_{th}$ order of the Bessel function, and $J_{2k}$ is the $(2k)^{th}$ order of the Bessel function. Similar expansions can be made for sin δ2 and cos δ2.

Substituting the expansions of sin δ1, cos δ1, sin δ2 and cos δ2 into equation (1) and taking only up to the second order of the Bessel function, we obtain the following parts:

$$P1 = 1 + [J_0(\delta 1_0) + 2J_2(\delta 1_0)\cos(2\omega_1 t)] \cdot [J_0(\delta 2_0) + \qquad \text{Eqn. (4.1)}$$
$$2J_2(\delta 2_0)\cos(2\omega_2 t)]\sin(4\rho)\sin^2\left(\frac{\delta}{2}\right)$$

$$P2 = 2J_1(\delta 1_0)\sin(\omega_1 t) \cdot 2J_1(\delta 2_0)\sin(\omega_2 t) \cdot \cos\delta \qquad \text{Eqn. (4.2)}$$

$$P3 = [J_0(\delta 1_0) + 2J_2(\delta 1_0)\cos(2\omega_1 t)] \cdot [2J_1(\delta 2_0)\sin(\omega_2 t)] \qquad \text{Eqn. (4.3)}$$
$$\cos(2\rho)\sin\delta$$
$$= J_0(\delta 1_0) \cdot 2J_1(\delta 2_0)\sin(\omega_2 t)\cos(2\rho)\sin\delta +$$
$$2J_2(\delta 1_0)\cos(2\omega_1 t) \cdot 2J_1(\delta 2_0)\sin(\omega_2 t)\cos(2\rho)\sin\delta$$

$$P4 = [J_0(\delta 2_0) + 2J_2(\delta 2_0)\cos(2\omega_2 t)] \cdot [2J_1(\delta 1_0)\sin(\omega_1 t)] \qquad \text{Eqn. (4.4)}$$
$$\sin(2\rho)\sin\delta$$
$$= J_0(\delta 2_0) \cdot 2J_1(\delta 1_0)\sin(\omega_1 t) \cdot \sin(2\rho)\sin\delta +$$
$$2J_2(\delta 2_0)\cos(2\omega_2 t) \cdot 2J_1(\delta 1_0)\sin(\omega_1 t)\sin(2\rho)\sin\delta$$

Equation (4.1) contains both AC and DC terms. The DC terms can be used to detect the average light intensity reaching the detector. Equation (4.2) is useful for determining linear retardation up to $\pi$ (i.e., half-wavelength or $\lambda/2$). Equations (4.3) and (4.4) can be used to determine linear retardation at low levels, such as below $\pi/2$ (quarter-wavelength or $\lambda/4$). For determining very small linear retardation, equations (4.3) and (4.4), compared with equation (4.2), give more accurate results by using the $\sin^{-1}$ function instead of the $\cos^{-1}$ function.

The DC signal can be derived from term (1) to be:

$$V_{DC} = \frac{KI_0}{2}\left\{1 + J_0(\delta 1_0) \cdot J_0(\delta 2_0) \cdot \sin(4\rho)\sin^2\left(\frac{\delta}{2}\right)\right\} \qquad \text{Eqn. (5)}$$

where any AC terms that vary as a function of the PEMs' modulation frequencies are omitted because they have no net contribution to the DC signal. The low-pass electronic filter 46 is used to eliminate such oscillations.

Figure 3:
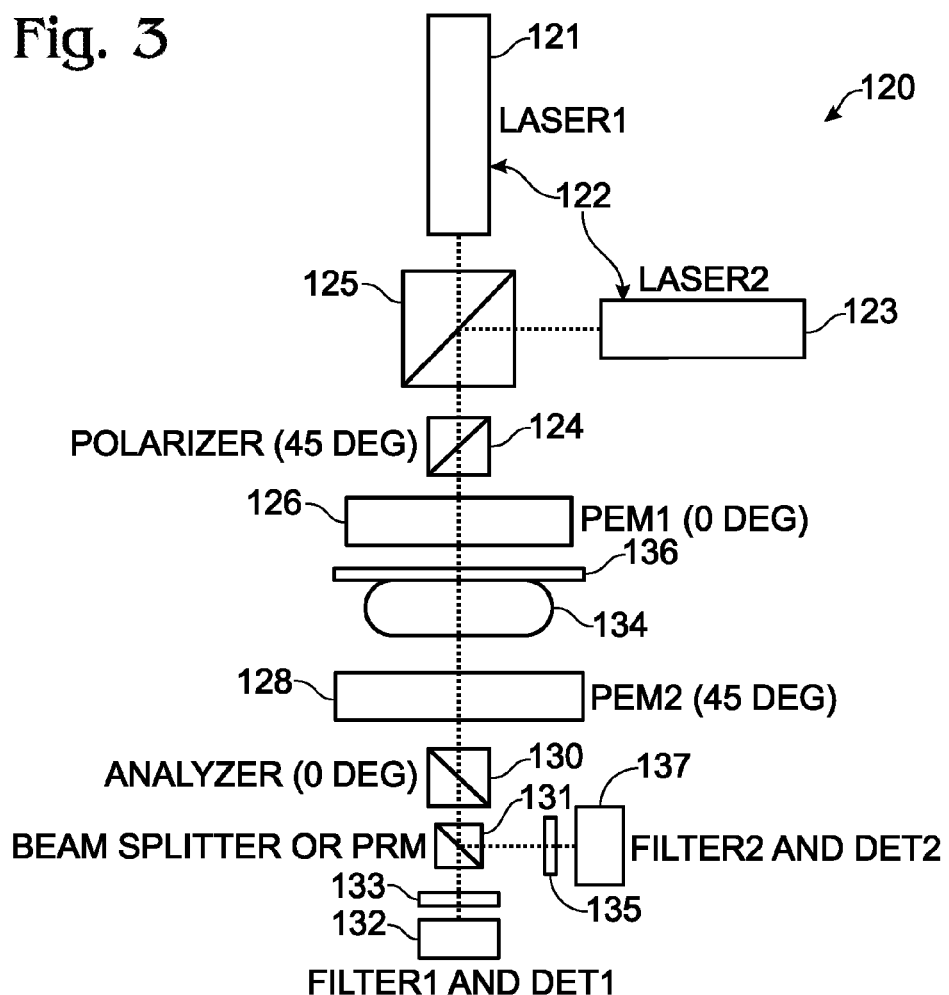
FIG. 3 is a diagram of another preferred embodiment of the present invention showing a preferred arrangement of the optical components of that system.

Within a small-angle approximation (i.e., sin X=X and $\sin^2$ X=0, when X is small), $V_{DC}$ is independent of the sample's retardation and thus represents the average light intensity reaching the detector. When a sample having a retardation level above 30 nm is measured, the $V_{DC}$ as shown in equation (5) will generally be affected by the magnitude and angle of the retardance. Thus, the measured DC signal will not be a true representation of the average light intensity. In this case, the most straightforward way to proceed is to set both $J_0(\delta 1_0)$ and $J_0(\delta 2_0)$ equal to "0". This method is discussed more below in connection with another preferred embodiment as depicted in FIG. 3.

As respects the low-level retardance measure of the present embodiment (FIGS. 1 and 2), different signals modulated at different harmonics of the two PEMs 26, 28 are measured as shown in equations (4.1)-(4.4) above. The modulated signals from the two PEMs can be measured using either the depicted lock-in amplifiers 40, 42 or conventional digital waveform sampling and analysis methods.

When lock-in amplifiers are used, proper reference signals of the two PEMs 26, 28 must be created. For example, determination of cos δ from equation (4.2) requires the reference signal of ($\omega_1+\omega_2$), and the determination of cos (2ρ)sin δ and sin(2ρ)sin δ from the latter terms in equations (4.3) and (4.4) requires the reference signal of ($2\omega_1+\omega_2$) and ($\omega_1+2\omega_2$).

Figure 4:
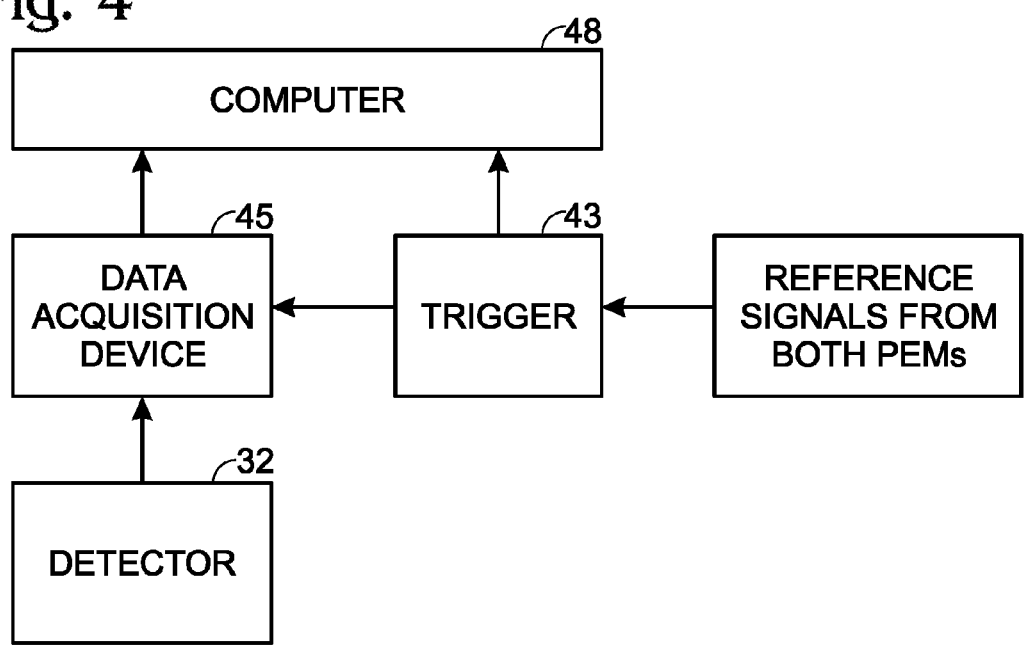
FIG. 4 is a block diagram of alternative processing components of the system.

With reference to FIG. 4, the above mentioned reference signals, ($\omega_1+\omega_2$), ($2\omega_1+\omega_2$) and ($\omega_1+2\omega_2$) are applied to a hardware trigger 43, which controls the sampling of a data acquisition device 45. That device 45 receives on its analog input the signal produced by the detector 32. The data acquisition device 45 includes analog-to-digital conversion components for delivering on its output to computer 48 digitized waveforms of the signal generated at the detector 32. The waveforms represent the combined result of both PEMs' modulation harmonics. The digitized waveform is then analyzed by Fourier transform at the above noted terms. For measuring linear birefringence up to half-wavelength of the light source, the same three terms are required as those appearing in equations (4.2)-(4.4):

($2\omega_1+\omega_2$) and ($\omega_1+2\omega_2$) terms:

$$V_{2\omega_1+\omega_2} = \frac{KI_0}{2}2J_2(\delta 1_0) \cdot 2J_1(\delta 2_0)\cos(2\rho)\sin\delta \qquad \text{Eqn. (5.1)}$$

$$V_{2\omega_2+\omega_1} = \frac{KI_0}{2}2J_2(\delta 2_0) \cdot 2J_1(\delta 1_0)\sin(2\rho)\sin\delta \qquad \text{Eqn. (5.2)}$$

($\omega_1+\omega_2$) term: \qquad \text{Eqn. 5.3}

$$V_{\omega_1+\omega_2} = \frac{KI_0}{2}2J_1(\delta 1_0) \cdot 2J_1(\delta 2_0) \cdot \cos\delta$$

In this embodiment, the PEMs' retardation amplitude was selected as $\delta 1_0=\delta 2_0=2.405$ radians (0.3828 waves) for recording the DC signal, which is independent of ρ and δ. That DC signal is:

$$V_{DC} = \frac{KI_0}{2} \qquad \text{Eqn. (6)}$$

In order to eliminate the effect of light intensity variations due to light source fluctuations and the absorption, reflection, and scattering from the sample and other optical components of the setup, the ratios of the AC signals to the DC signal are used. The ratios of the AC signals to the DC signal for the ($2\omega_1+\omega_2$), ($\omega_1+2\omega_2$) and ($\omega_1+\omega_2$) terms are represented in equations (7.1)-(7.3):

$$\frac{V_{2\omega_1+\omega_2}}{V_{DC}} = 2J_2(\delta 1_0) \cdot 2J_1(\delta 2_0)\cos(2\rho)\sin\delta \qquad \text{Eqn. (7.1)}$$

$$\frac{V_{2\omega_2+\omega_1}}{V_{DC}} = 2J_2(\delta 2_0) \cdot 2J_1(\delta 1_0)\sin(2\rho)\sin\delta \qquad \text{Eqn. (7.2)}$$

$$\frac{V_{\omega_1+\omega_2}}{V_{DC}} = 2J_1(\delta 1_0) \cdot 2J_1(\delta 2_0)\cos\delta. \qquad \text{Eqn. (7.3)}$$

Defining $R_1$, $R_2$ and $R_3$ as corrected ratios, equations (7.1)-(7.3) become:

$$\frac{V_{2\omega_1+\omega_2}}{V_{DC}}\frac{1}{2J_2(\delta 1_0) \cdot 2J_1(\delta 2_0)} = R_1 = \cos(2\rho)\sin\delta \qquad \text{Eqn. (8.1)}$$

$$\frac{V_{2\omega_2+\omega_1}}{V_{DC}}\frac{1}{2J_2(\delta 2_0) \cdot 2J_1(\delta 1_0)} = R_2 = \sin(2\rho)\sin\delta \qquad \text{Eqn. (8.2)}$$

$$\frac{V_{\omega_1+\omega_2}}{V_{DC}}\frac{1}{2J_1(\delta 1_0) \cdot 2J_1(\delta 2_0)} = R_3 = \cos\delta. \qquad \text{Eqn. (8.3)}$$

Finally, by dividing $R_1$ and $R_2$ by $R_3$ and rearranging equations (8.1)-(8.3), the retardation magnitude and angle of fast axis of the sample is expressed as:

$$\rho = \frac{1}{2}\tan^{-1}\left[\frac{R_2}{R_1}\right] \text{ or } \rho = \frac{1}{2}ctg^{-1}\left[\frac{R_1}{R_2}\right] \quad \text{Eqn. (9.1)}$$

$$\delta = \tan^{-1}\left(\sqrt{\left(\frac{R_1}{R_3}\right)^2 + \left(\frac{R_2}{R_3}\right)^2}\right) \text{ or } \delta = \cos^{-1} R_3 \quad \text{Eqn. (9.2)}$$

where $\delta$, represented in radians, is a scalar. When measured at a specific wavelength (i.e. 632.8 nm), $\delta$ can be converted to retardation in "nm" ($\delta_{nm} = \delta_{rad} \cdot 632.8/(2\pi)$).

Using the sign information of the raw data, equations (9.1) and (9.2) lead to unambiguous determination for both the magnitude and angle of fast axis of linear retardation in the range of $0-\pi$ (half wave).

When the actual retardation is between $\pi$ and $2\pi$, the present embodiment will report a retardation value between 0 and $\pi$ and an angle of fast axis that is shifted by 90°. This results in an apparently severe error for retardation between $\pi$ and $2\pi$. However, since the Mueller matrices are identical for both ($\delta$, $\rho$) and ($\lambda-\delta$, 90°+$\rho$), this seemingly large error has no practical consequences for optical systems that can be modeled by Mueller matrices.

The signals at the modulation frequencies of ($2\omega_1+\omega_2$) and ($\omega_1+2\omega_2$) depend on the orientation of the fast axis of the sample (see equation (5)), and the final retardation magnitudes are independent of the fast axis angles (see equation (9)). To achieve this angular independence of retardation magnitude, it is important to accurately orient all optical components in the system (as well as those of the embodiments described below). When the optical components are misaligned, retardation magnitude shows specific patterns of angular dependence. The first PEM's optical axis is used as the system reference angle ("0°"). All other optical components in the system are accurately aligned directly or indirectly with this reference angle.

When the sample under consideration is a stretched polymer film, the direction of the fast (or slow) axis of the film is established, since the orientation direction of the stretched film corresponds to either the fast axis or the slow axis. Thus, the measured angle of the fast axis will be either 0 degrees or 90 degrees. Given this information, the current embodiment of the birefringence measuring system for stretched polymer films can be extended to determine retardation levels between zero and an upper level corresponding to the full wavelength of the light source of the system.

Figure 6:
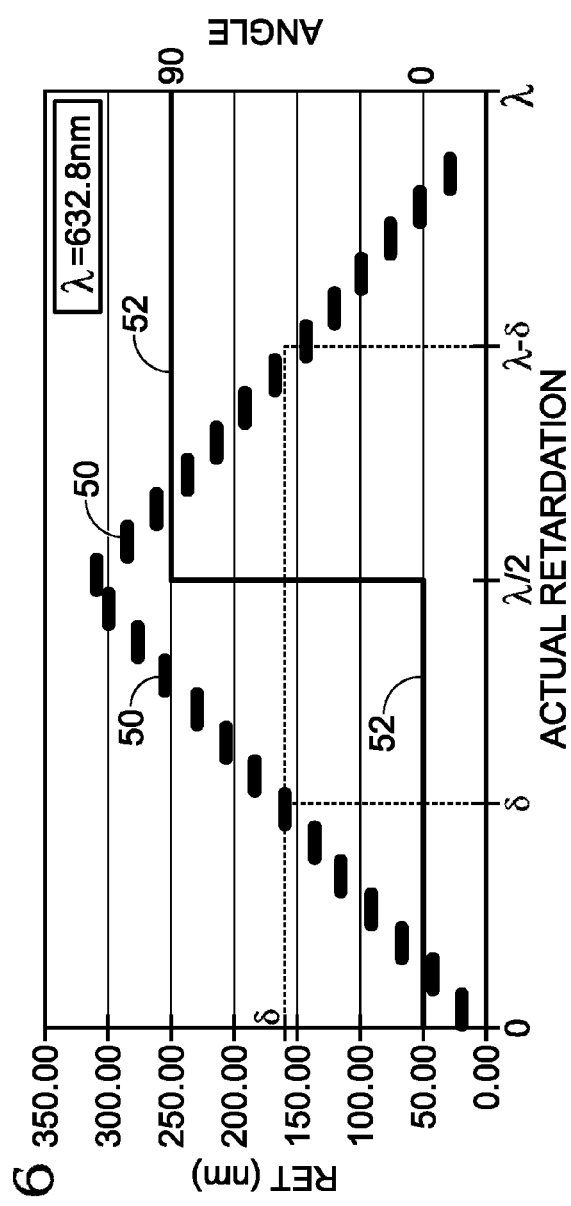
FIG. 6 is a graph depicting actual versus measured retardance values for an optical sample having a known orientation of its fast axis angle.

The validity of this determination can be demonstrated when one considers FIG. 6, which graphically illustrates the retardation values 50 and fast axis angle 52 of a Soleil-Babinet compensator that is employed as a sample and that is operated to vary the retardation values from 0 to a full wavelength ($\lambda$) of the light source (633 nm laser). One can observe from FIG. 6 that the measured retardation values (corresponding to the left, vertical axis of the graph) decrease from one-half of the wavelength to zero across the right side of the graph, where the actual retardation values (horizontal axis) change from one-half of the wavelength ($\lambda/2$) to one full wavelength ($\lambda$). One also notes that the angle of fast axis (considering the rightmost, vertical axis of the graph) changes by 90 degrees at the location where the actual retardation value corresponds to the one-half wavelength level.

As noted above, the current embodiment of the birefringence measuring system for stretched polymer films can be extended to determine retardation levels between zero and an upper level corresponding to the full wavelength of the light source of the system. To this end, the stretched polymer film sample is physically oriented with its known fast axis direction deliberately aligned with the 0° or 90° reference angle of the optical setup. The alignment need not be precise, but, preferably, the fast axis should be aligned to be within ±45° of the system reference angle (although the system will treat an axis within this range as aligned for computational purposes). It is thus apparent that the system has a very high tolerance for sample alignment errors.

With the fast axis of the stretched polymer film so aligned, the system will thus have as an input parameter a known value for $\rho$. Given a stretched film's actual-versus-measured retardation characteristics across one wavelength (which will generally match what is shown in the graph of FIG. 6) the measured values of the retardance (vertical axis) will be the same at $\delta$ and at ($\lambda-\delta$) (horizontal axis). Thus, the retardation level, either $\delta$ or ($\lambda-\delta$), that corresponds to the known, previously input axis alignment location, either $\pi$ or (90°+$\rho$), is retained by the system as the actual retardation level.

In order to accurately measure low-level linear birefringence, it is important to correct for the existing residual linear birefringence of the optical setup itself ("instrument offset") even when high quality optical components are used.

The instrument offset is primarily due to the small residual linear birefringence in the PEMs (on the order of 0.1 nm). To correct for the instrument offset, an average of several measurements without any sample is first obtained. The instrument offsets are corrected in software when a sample is measured. Such corrections should only be done when the ratios are calculated using equations (8), not on the final results of $\delta$ and $\rho$, as determined in equations (9). The instrument offsets should be constants (within the instrumental noise level) unless there is a change in either the alignment of optical components or laboratory conditions such as temperature. It is prudent to check the instrument offsets with some regularity.

This offset correction works within the limit of small retardance when the Mueller matrices of retardance commute. In practice, this may be the only case where an offset correction is needed. Since the residual retardation in the PEMs is so small (on the order of 0.1 nm), offset correction may not be necessary when measuring retardation higher than 50 nm.

The next described embodiment, the setup for which is illustrated in FIG. 3, is suitable for accurate and rapid measurements of high levels of retardance in samples, such as stretched polymer films, that have a known fast axis angle. With reference to FIG. 3, the optical setup 120 for this embodiment in many respects matches that described in connection with FIG. 1. The setup 120 includes a light source 122 for directing a beam 127 of light through the system. The particulars of the light source are described more below. The setup 120 may be vertically oriented with the beam 127 propagating downwardly (FIG. 1). A vertical orientation of the setup is described here for the purpose of easily specifying the relative positions of the various optical components, but the setup orientation is not otherwise important.

The setup 120 also includes a polarizer 124 oriented at 45 degrees, as well as a first PEM 126 with its optical axis at 0 degrees. A second PEM 128 that is set to a different modulation frequency (than the first PEM) is oriented at 45 degrees, and an analyzer 130 that is oriented at 0 degrees follows (in the path of the light beam 127) the second PEM 128.

In this embodiment, the light source provides a light beam 127 that is a composite of two beams from individual sources. Specifically, the light source 122 includes a first laser 121, such as a He—Ne laser, that operates at a wavelength $\lambda_1$ of, for example, 543.5 nm. The source also includes a second laser 123 that operates at a different wavelength $\lambda_2$ of, for example, 632.8 nm. The output of each laser 121, 123 is directed, as shown in FIG. 3, through and reflected off, respectively, a partial refection mirror 125 so that the single, composite beam 127 emanates from the downward facing surface of that mirror 125.

The beam 127 is thus directed through the polarizer 124, PEM 126 and through the polymeric film sample 136, which may be supported as needed by a sample support 134 that permits the beam 127 emanating from the sample 136 to continue through the second PEM 128 and analyzer 130. The beam 127 is then directed through a dichroic, partial reflection mirror that is arranged to act as a beam splitter that permits passage of the wavelength of the first laser 121 into a detector 132, and that reflects the wavelength of the second laser 123 into another detector 137. Preferably, a filter 133, 135 is located at the inlet of each detector to more precisely select the particular wavelengths that are directed to each detector 132, 137.

The output for each detector 132, 137 is processed as described above in connection the output of detector 32 (see FIG. 2) in the embodiment of FIG. 1. In accord with the embodiment of FIG. 3, the angle of the fast axis of the stretched polymer film is known and aligned with the system as described above. Thus, as provided in equation (5.3) above, the DC signal is:

$$V_{DC} = \frac{KI_0}{2}\left\{1 + J_0(\delta 1_0) \cdot J_0(\delta 2_0) \cdot \sin(4\rho)\sin^2\left(\frac{\delta}{2}\right)\right\} \quad \text{Eqn. (5.3)}$$

As mentioned above, to accurately measure birefringence of a sample, the DC signal needs to be independent of the retardation value and angle of fast axis. Namely, the second term of in equation (5.3) must be set to zero, or:

$$J_0(\delta 1_0) \cdot J_0(\delta 2_0) \cdot \sin(4\rho)\sin^2\left(\frac{\delta}{2}\right) = 0 \quad \text{Eqn. (5.3.1)}$$

Theoretically, and in the absence of the small angle approximation that was suitable for the low-level birefringence measurement discussed above, this condition is satisfied if any of the four terms in equation (5.3.1) is "0." Therefore, in addition to setting or aligning the fast axis angle of the stretched polymer sample as close to "0" degree as possible, the $J_0$ terms in equation (5.3.1) should also be close to "0". Considering the FIG. 3 setup, what follows is an algorithm carried out using the components of the setup 120 for setting the $J_0$ terms in equation (5.3.1) to be close to "0".

1. Sample Used for Setting the $J_0$ Terms:
The sample used here should be close to a quarter-wave plate for both wavelengths ($\lambda_1$, $\lambda_2$) used in the FIG. 3 setup as described above. A $0^{th}$ order quarter-wave plate designed for a wavelength that is close to the wavelengths used in the setup will work well for this purpose.

2. Modulated Signals Used in Setting the $J_0$ Terms:

The first harmonic signals of both PEMs 126, 128 used in the setup are monitored for setting the PEMs' driving voltages that make $J_0 \approx 0$. The modulated signals from the two PEMs can be measured using either lock-in amplifiers or waveform analysis methods.

3. Setting the PEMs' Driving Voltages:

a. The system must first be calibrated and tested at each wavelength. This can be done, for example, by simply blocking one of the two light beams emanating from lasers 121 or 123. This step accurately determines the driving voltage of each PEM that makes $J_0=0$. The four determined quantities determined in this step are:

PEM1W1V: the driving voltage of PEM 126 that gives $J_0=0$ for PEM 126 at wavelength $\lambda_1$;

PEM2W1V: the driving voltage of PEM 128 that gives $J_0=0$ for PEM 128 at wavelength $\lambda_1$;

PEM1W2V: the driving voltage of PEM 126 that gives $J_0=0$ for PEM 126 at wavelength $\lambda_2$; and PEM2W2V: the driving voltage of PEM 128 that gives $J_0=0$ for PEM 128 at wavelength $\lambda_2$.

b. In the system of FIG. 3 for measuring high levels of birefringence in stretched polymers, the following quantities are employed:

PEM1W1V: the driving voltage of PEM 126 that gives $J_0=0$ for PEM 126 at wavelength $\lambda_1$; and PEM2W2V: the driving voltage of PEM 128 that gives $J_0=0$ for PEM 128 at wavelength $\lambda_2$.

When the values of the wavelengths of the two light sources 121, 123 used in the setup 120 are close to one another, the use of PEM1W1V and PEM2W2V as just noted will ensure that one of the two $J_0$ terms is accurately set at "0" while the other one is close to "0." Therefore the product of the four terms in equation (5.3.1) is always "0" with good approximation.

With the product of the four terms of equation (5.3.1) thus established at zero, equations (9.1)-(9.2) are validly applied for calculating the retardation in the FIG. 3 embodiment. Assuming that the birefringence dispersion of the stretched polymeric film being measured is negligible at the two different wavelengths, the relationship between the actual retardation and the measured retardation for the first several full wavelength cycles is:

$$m\lambda_1+\delta_1=m\lambda_2+\delta_2 \text{ when } (\delta_1-\delta_2)>=0 \; m\lambda_1+\delta_1=(m-1)\lambda_2+\delta_2 \text{ when } (\delta_1-\delta_2)<0 \quad \text{Eqn. (10)}$$

where $\lambda_1$ and $\lambda_2$ ($\lambda_1<\lambda_2$) are the two wavelengths of the light sources 121, 123; $\delta_1$ and $\delta_2$ are the measured retardation values after the full wavelength conversion at $\lambda_1$ and $\lambda_2$, respectively; m is an integer (m>=0) representing the number of full wavelength of the shorter wavelength included in the actual retardation.

From equation (10), we can calculate m as:

$$m=(\delta_1-\delta_2)/(\lambda_2-\lambda_1) \text{ when } (\delta_1-\delta_2)>=0, \text{ or } m=[(\delta_1-\delta_2)+\lambda_2]/(\lambda_2-\lambda_1) \text{ when } (\delta_1-\delta_2)< \quad \text{Eqn. (11)}$$

The actual retardation of the sample 136 is then determined by:

$$\text{Re}t(\text{nm}) = m\lambda_1 + \delta_1 = \frac{\lambda_1(\delta_1 - \delta_2)}{(\lambda_2 - \lambda_1)} + \delta_1 \qquad \text{Eqn. (12)}$$

$$= m\lambda_2 + \delta_2 = \frac{\lambda_2(\delta_1 - \delta_2)}{(\lambda_2 - \lambda_1)} + \delta_2$$

when $(\delta_1 - \delta_2) >= 0$, or $$\text{Re}t(\text{nm}) = m\lambda_1 + \delta_1 = \frac{\lambda_1[(\delta_1 - \delta_2) + \lambda_2]}{(\lambda_2 - \lambda_1)} + \delta_1$$

$$= (m-1)\lambda_2 + \delta_2 = \frac{\lambda_2[(\delta_1 - \delta_2) + \lambda_1]}{(\lambda_2 - \lambda_1)} + \delta_2$$

when $(\delta_1 - \delta_2) < 0$

Figure 5:
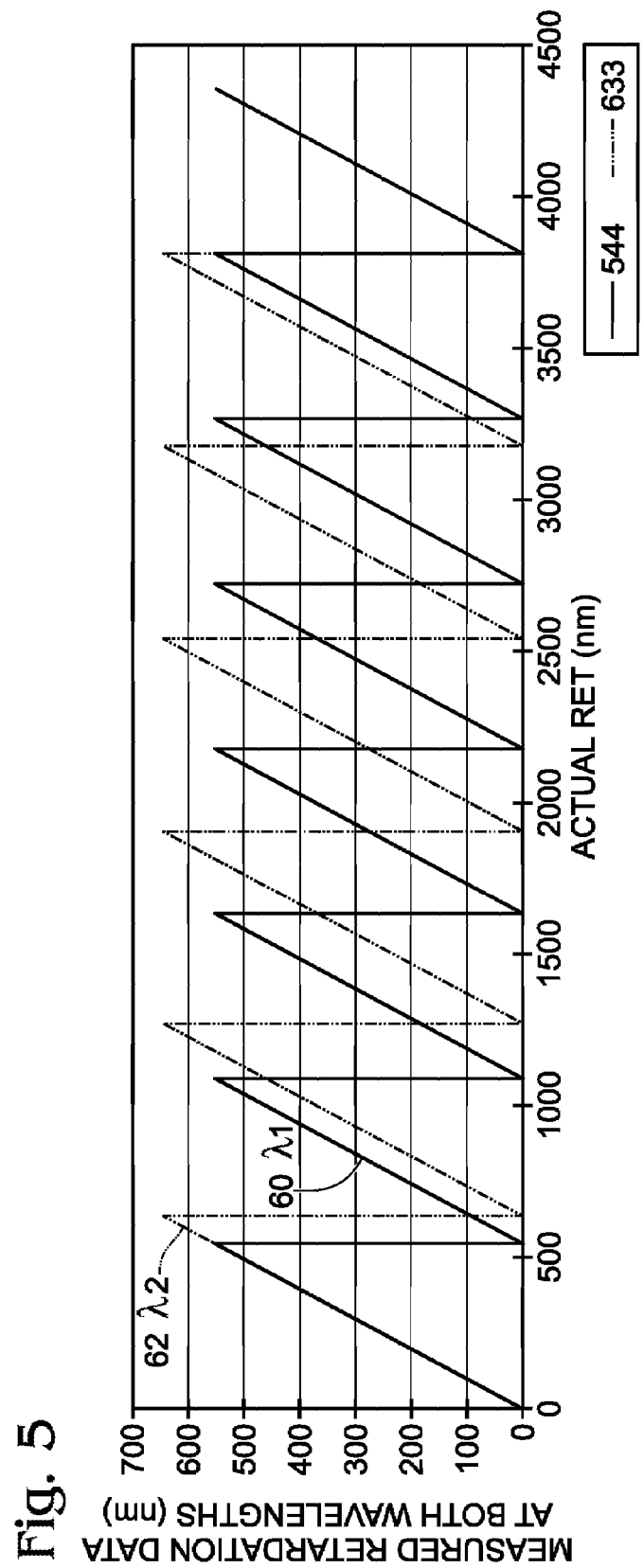
FIG. 5 is graph depicting retardation curves for a sample that is measured at two different wavelengths in accord with one aspect of the present invention.

When two wavelengths ($\lambda_1$ and $\lambda_2$) are used for the retardation measurement, the possible measurements that are based on these wavelengths are illustrated in the graph of FIG. 5 as solid line 60 and dashed line 62 respectively. That is, FIG. 5 shows possible retardation measurements of the FIG. 3 system in which two He—Ne lasers, operating at wavelengths of 543.5 nm and 632.8 nm, respectively, are employed. The graph of FIG. 5 illustrates the relationship between the measured retardation values at 543.5 nm and 632.8 nm and the actual retardation in the range from 0 to approximately 4,300 nm.

Figure 7:
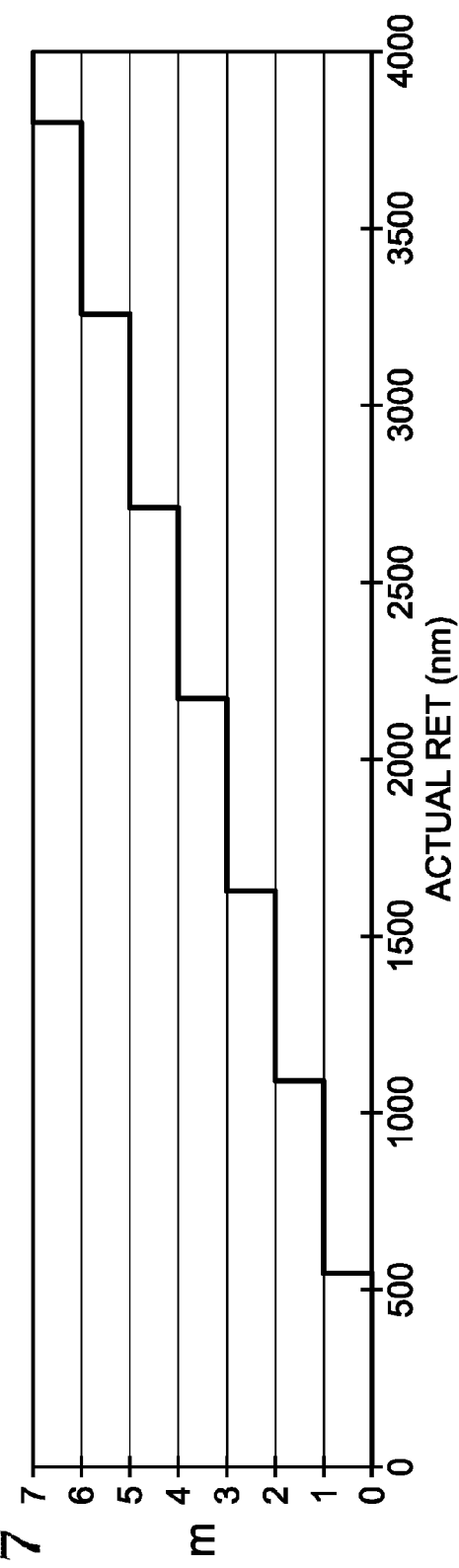
FIG. 7 is a graph depicting the values of a variable "m" that is used in calculating the high levels of birefringence in a stretched polymer film.

Using the data illustrated in FIG. 5 one can calculate and determine values for "m" using equation (11), the results of this calculation are depicted in FIG. 7.

Returning to FIG. 5, the two curves 60, 62 represent retardation values, which can be measured using the two selected wavelengths, in the range of 0-4,300 nm. After seven cycles of the $\lambda 1$ curve (543.5 nm) and six cycles of the $\lambda 2$ curve (632.8 nm), the two curves come close to overlapping, but with $\lambda 1$ curve leading by 7.7 nm (543.5×7−632.8×6=7.7). After 14 cycles of the $\lambda 1$ curve and 12 cycles of the $\lambda 2$ curve, the two curves come close again, but with the $\lambda 1$ curve leading $\lambda 2$ curve by 15.4 nm. Similarly, the $\lambda 1$ curve will lead the $\lambda 2$ curve by 23.1 nm (3×7.7 nm) after three revolutions of this combined seven/six cycle process.

This seven/six cycle will continue, with each cycle being unique (i.e., no overlap with resulting ambiguity in the measured data). Consequently, the actual retardation can be determined for each seven/six cycle using equations that differ only slightly from equation (12). Therefore, the upper retardation limit of this method, which is dependent on the values of the two wavelengths selected, is the product of the two wavelengths $\lambda 1$ and $\lambda 2$ (543.5×632.8=343,926.8).

It is noteworthy that since the wavelengths of the He—Ne gas lasers 121, 123 are determined by atomic electron transitions, the separate-wavelength outputs of the gas lasers are extremely accurate. The upper retardation limit of this method is usually a product of the two wavelengths, which thus provides very high retardation measurement limits. In practice, measurement errors will dictate the upper retardation limits. For example, if the measurement system has an error that is close or larger than 7.7 nm in the example above, the experimental error will make it impractical to distinguish between the first and second seven/six cycles. The retardation limit will then be about 3,800 nm.

If the He—Ne laser pair 121, 123 is selected so that $\lambda 1$ is 611.8 nm and $\lambda 2$ is very close to that, such as 632.8 nm (these being commonly used lasers), after 30 wavelength cycles of 611.8 nm and 29 cycles of 632.8 nm, the two curves would come within 16 nm of one another, which is still distinguishable in the PEM-based high level birefringence measurement system of the present invention. Even without extending to the second 30/29 wavelength cycle, the retardation upper limit would be at least about 18,000 nm (632.8×29=18,351).

Accordingly, by properly selecting the laser pairs, one can achieve practical retardation upper limits from several thousands of nanometers to tens of thousands of nanometers. Furthermore, in the rare instance where the laser pair gives ambiguous results, one can use a third laser to distinguish the measurement results and to extend the measurement range.

It is also possible to select a pair of wavelengths for each light source 121, 123 that are a ratio of their integers. For example, one could select the two wavelengths to have an exact 6-to-5 ratio. In such cases, the six/five wavelength cycle will repeat exactly. In this case, the upper retardation limit will be precisely five times the longer wavelength (or six times the shorter wavelength).

A He—Ne laser pair consisting of the red (632.8 nm) and yellow (587.6 nm) wavelengths provides a nearly exact 13 to 14 wavelength cycle (13×632.8=8,226.4; 14×587.6=8,226.4). Therefore, a high level birefringence measurement system built using this laser pair will have an upper retardation limit of 8,226 nm. As a practical matter, one would be limited to distinguishing retardation values within the retardation range of 0-8,226.4 nm using such a system.

It is noteworthy here that although one light source 122 was described above as including two separate lasers 121, 123, other light source configurations are contemplated in this embodiment. For example, a single laser that produces two distinct wavelengths may be used. One such example might be a tunable diode laser. Another example is a HeCd laser that is operable to produce beams of 325 nm and 442 nm wavelengths. Air-cooled ion lasers that simultaneously produce two or three output beams at, for example, 488 nm, 568 nm, and 647 nm, may also be employed.

As another alternative, the light source 122 could be a broadband lamp with associated collimating optics. The broadband light source (such as a mercury, xenon, or deuterium lamp) would be combined with a filter wheel or wheels to select the desired wavelengths. Different types of optical filters, including high-pass, low-pass, and band pass filters, can be used in the filter wheel. A combination of filter wheels can be applied when necessary.

It is also contemplated that optical fiber(s) could be used to direct the light from the source to the other components (such as the polarizer 124 and PEM 126) of the setup 120.

It is also contemplated that alternative detector arrangements can be used. For example, with reference to FIG. 3, the beam emanating from the analyzer 130 could be directed through a prism or other color (wavelength) separating device for thus separating the beam into two beams having the two wavelengths of interest. The separated beams are then individually directed to the detectors 132, 137.

It is noteworthy that with stretched polymeric films the level of intrinsic retardance can vary significantly across a very short distance of the film. For example, depending upon the degree of stretch applied to the film (normally expressed as a ratio or "stretching factor," such as 5-to-1), measured retardation values can vary by up to hundreds of nanometers within just a few millimeters of the measurement locations on the film. Accordingly, the two beams that make up the composite beam 127 must be precisely aligned in space (that is, have a common central axis and beam diameter) to avoid errors that may otherwise be induced should the beams diverge slightly in propagating through a sample that has the steep variations in retardance levels as just noted. Moreover, in instances where the film is moved relative to the beam, it is important to ensure that the beam components propagate in an integrated, simultaneous fashion (rather than sequentially) to ensure both components of the beam strike the same location on the sample at the same time.

Returning to FIG. 2, a computer 48 is used to control and coordinate the selection of wavelengths from the light source(s), as well as driving the PEMs at an optimal level for measuring birefringence, collecting data returned by the detection processing components described above, and calculating the final results. The computer includes a display for presenting the retardation results, which are also recorded for later use. Alarms and process control components may also be associated with the computer in instances where departures from expected birefringence values may require changes to the polymeric film production process.

Any of a number of variations for displaying the measured data will suffice. The resulting data can be conveniently, interactively displayed. It will also be apparent that the user of the system will have available suitable user input means for setting operating parameters of the system (scan boundaries, grid spacing, sample thickness, sample movement speed, etc.).

While the present invention has been described in terms of preferred embodiments, it will be appreciated by one of ordinary skill in the art that modifications may be made without departing from the teachings and spirit of the foregoing. For example, a single-PEM, single-detector system such as described in U.S. Pat. No. 6,473,179 (hereafter the '179 system" and hereby incorporated by reference), and using one of the two detection channels described there as well as a dual wavelength light source as described above can be used for retardance measurement of stretched polymer film samples in which the angle of fast axis is known and aligned with the reference angle of the '179 system.

Finally, it is worth mentioning when using the system for measuring high levels of birefringence described (based upon the knowledge of the fast axis angle of a stretched polymer sample), a correction must be applied in the situation when no sample is present in the setup or when the sample has an extremely low level of retardation. The measured fast axis angle will be nearly random at a low retardation level that approaches the noise level of the system. If it is not corrected properly, the uncorrected system would report a very low retardation value when the angle of fast axis is close to "0" degrees and report a retardation value that is close to the full wavelength of the light source when the angle of the fast axis is close to 90 degrees. Accordingly, the computer program for carrying out the calculations described above compares the retardation levels measured at both wavelengths and if those levels are extremely low, disregards the angle of fast axis in the measurement.

Finally, if the birefringence dispersion of the stretched polymeric film being measured is significant at the two different wavelengths, the equations 10-12 can be modified slightly to account for the dispersion effect.

The invention claimed is:

1. A method of determining the birefringence level of a sample of optical material using a setup of optical components that has a known system reference angle, wherein the sample has a fast axis angle having a predetermined orientation in the sample, the method comprising the steps of:
   aligning the direction of the fast axis of the sample to coincide substantially with the reference angle of the system; and
   measuring the birefringence level at a location on the sample.

2. The method of claim 1 wherein measuring includes separately directing through the sample a first beam of polarization-modulated light having a first wavelength and a second beam of polarization-modulated light having a second wavelength, the first and second wavelengths being different.

3. The method of claim 2 wherein the first and second wavelengths are selected to provide unambiguous measure of birefringence at levels greater than one full first wavelength.

4. The method of claim 2 wherein the first and second wavelengths are selected to provide unambiguous measure of birefringence at levels in the range of zero to several multiples of one of the first or second wavelengths.

5. The method of claim 2 wherein the first and second wavelengths are selected to provide unambiguous measure of birefringence at levels in the range of zero to about 4,300 nm.

6. The method of claim 2 wherein the first and second wavelengths are selected to provide unambiguous measure of birefringence at levels in the range of zero to about 18,000 nm.

7. The method of claim 2 wherein the first and second wavelengths are selected to be a predetermined ratio of each other.

8. The method of claim 2 including the step of directing the first and second beams through the same location on the sample.

9. The method of claim 8 wherein directing includes arranging a partially reflective member between two discrete sources of light and the sample.

10. The method of claim 9 including the step of separating the two beams after the beams pass through the sample.

11. The method of claim 9 including the step of simultaneously directing the first and second beams through the same location in the sample.

12. The method of claim 2 wherein measuring includes separately directing through the sample a third beam of polarization-modulated light having a third wavelength, the first and second and third wavelengths being different.

13. The method of claim 1 including the step of supporting the sample for movement relative to the beams.

14. The method of claim 1 including the step of providing a stretched polymeric film as the sample.

15. The method of claim 1 including the step of collecting for display or recording data representative of the measure of the birefringence level at the location on the sample.

16. A system for measuring birefringence levels in a sample of optical material that has a fast angle axis with a known orientation, comprising:
   a source of two or more beams of light having respective first and second wavelengths that are different from one another;
   a polarization modulator for modulating the polarization of the light beams;
   a sample support for supporting the sample with its fast axis angle at a predetermined orientation; and
   measurement means for directing the beams through the sample and calculating the birefringence level of the sample.

17. The system of claim 16 wherein the source includes at least two discrete lasers.

18. The system of claim 16 wherein the source includes a single laser that is operable to produce two or more beams having different wavelengths.

19. The system of claim 16 wherein the source is a suitably filtered broadband lamp.

20. The system of claim 16 wherein the measurement means includes selection means to provide unambiguous measure of birefringence at levels greater than one full second wavelength.

21. The system of claim 16 wherein the measurement means includes selection means to provide unambiguous measure of retardation at levels in the range of zero to several multiples of the second wavelength.

22. The system of claim 16 wherein the measurement means includes selection means to provide unambiguous measure of retardation at levels in the range of zero to about 4,300 nm.

23. The system of claim 16 wherein the measurement means includes selection means to provide unambiguous measure of retardation at levels in the range of zero to about 18,000 nm.

24. The system of claim 16 wherein the sample is a stretched polymeric film.

\* \* \* \* \*